United States Patent [19]

Motta

[11] 4,267,323
[45] May 12, 1981

[54] HETEROCYCLIC CHEMICAL COMPOUND 6-PHENYL-[1,2,3]-OXADIAZOLO-(4,5 D)-PYRIDAZINE-7(6H)-ONE AND PROCESS FOR PRODUCING IT

[75] Inventor: Raimondo Motta, Milan, Italy

[73] Assignee: Oxon Italia S.p.A., Milan, Italy

[21] Appl. No.: 56,400

[22] Filed: Jul. 10, 1979

[30] Foreign Application Priority Data

Jul. 28, 1978 [IT] Italy .............................. 26230 A/78

[51] Int. Cl.³ ................. C07D 498/04; C07D 237/02; A61K 31/50
[52] U.S. Cl. ..................................... 544/236; 544/240
[58] Field of Search ....................... 544/236, 241, 240

[56] References Cited

PUBLICATIONS

Peters et al., J. Chem. Soc. 1943, 233.

Primary Examiner—Mark L. Berch

Attorney, Agent, or Firm—Young & Thompson

[57] ABSTRACT

A new heterocyclic chemical compound useful in the field of agricultural applications and in that of coloring substances has the formula

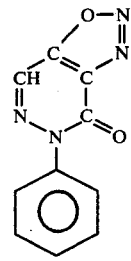

(6-phenyl-[1,2,3]-oxadiazolo-(4,5 d)-pyridazine-7(6H)-one).

3 Claims, No Drawings

HETEROCYCLIC CHEMICAL COMPOUND 6-PHENYL-[1,2,3]-OXADIAZOLO-(4,5 D)-PYRIDAZINE-7(6H)-ONE AND PROCESS FOR PRODUCING IT

SUMMARY OF THE INVENTION

The present invention relates to a heterocyclic chemical compound unknown up to today in the art and in literature and for which interesting uses are anticipated in various industrial fields, principally in the field of agricultural applications and in that of colouring substances.

The present invention relates more specifically to the heterocyclic chemical compound 6-phenyl-[1,2,3]-oxadiazolo-(4,5 d)-pyridazine-7(6H)-one having the formula:

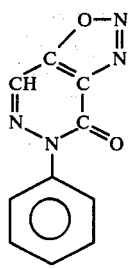

The compound which is the subject of the invention can be obtained by a process which also forms part of the present invention and which is characterized in that 5-chloro-4-amino-2-phenyl-3(2H)-pyridazinone is reacted with sodium nitrite in hydrochloric acid in accordance with the following reaction:

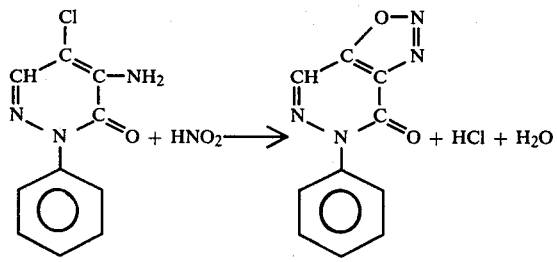

subsequent dilution with water and filtration being then provided.

DESCRIPTION OF THE PREFERRED EMBODIMENT

It has been possible to observe, in fact, that by carrying out the reaction given above and effecting the subsequent dilution with water, there occurs both diazotization of the amino group of the starting product and elimination of hydrochloric acid, with closing of the ring and precipitation of the compound 6-phenyl-[1,2,3]-oxadiazolo-(4,5 d)-pyridazine-7(6H)-one according to the invention, which is isolated by filtration.

This compound has a melting point of 113°-114° C., is soluble in ordinary organic solvents such as acetone, toluene, benzene, chloroform, alcohols and so on, is practically insoluble in water and, on the other hand, dissolves in concentrated hydrochloric acid. It is not stable in alkaline medium. Its structure has been confirmed by centesimal analysis, examination of the IR spectrum, spectroscopic investigation carried out via $H^1$ NMR and $C^{13}$ NMR, and mass analysis. It is considered that it can find wide applications in various industrial fields and especially in that of plant remedies, colouring substances or dyes and pharmaceuticals.

The invention is further illustrated by the following example of synthesis, which is nevertheless given purely for the purposes of example and is non-limitative.

EXAMPLE OF SYNTHESIS

In a reaction vessel there are placed:
1000 ml of 37% HCl
and then
111 g of 5-chloro-4-amino-2phenyl-3(2H)-pyridazinone. Dissolution is complete.

Diazotization is carried out between −10° C. and 0° C. by adding drop by drop a solution of 38 g of NaNO₂ in 250 ml of water.

At the end of the addition, maintaining takes place for half an hour. Dilution is then carried out with 1000 ml of water, cooling being effected. After maintaining, the precipitate is filtered off, washed to neutrality with water and dried.

93 g of the product according to the invention, 6-phenyl-[1,2,3]-oxadiazolo-(4,5 d)-pyridazine-7(6H)-one, having the formula:

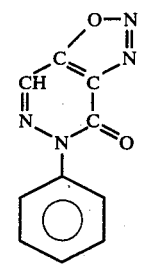

are obtained, giving a yield of 87% of the theoretical. The crystallized compound according to the invention has a melting point of 113°-114° C. Its centesimal analysis provides the following data:

| C | H | N | O |
|---|---|---|---|
| theor. 55.9% (56.07) | 2.75% (2.8) | 25.9% (26.16) | 15.45% (14.95) |

I claim:
1. Heterocyclic chemical compound 6-phenyl-[1,2,3]-oxadiazolo-(4,5 d)-pyridazine-7(6H)-one having the formula:

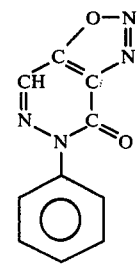

2. Process for obtaining the heterocyclic chemical compound 6-phenyl-[1,2,3]-oxadiazolo-(4,5 d)-pyridazine-7(6H)-one as claimed in claim 1, characterized in the 5-chloro-4-amino-2-phenyl-3(2H)-pyridazinone is reacted with sodium nitrite in hydrochloric acid in accordance with the following reaction:

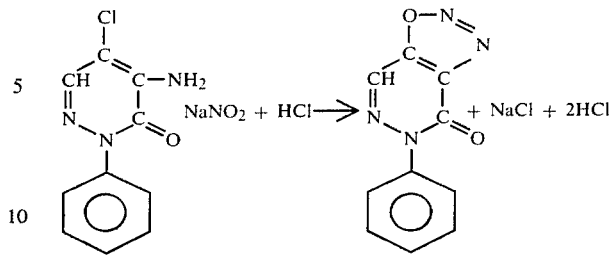

subsequent dilution with water and filtration being then provided.

3. Process as claimed in claim 2, wherein hydrochloric acid and 5-chloro-4-amino-2-phenyl-3(2H)-pyridazinone are placed in a reaction vessel, complete dissolution is carried out, diazotization is carried out between −10° C. and 0° C. by adding a solution of NaNO₂ in water drop by drop, maintaining for about half and hour and dilution with water is carried out, the precipitate being then filtered off and finally washed to neutral pH with water and dried.

* * * * *